(12) United States Patent
Steven

(10) Patent No.: US 6,898,810 B2
(45) Date of Patent: May 31, 2005

(54) MEDICAL TABLE EXTENSION AND METHOD

(75) Inventor: Peter M. Steven, Salt Lake City, UT (US)

(73) Assignee: Morphographics, P.C., Salt Lake City, UT (US)

( * ) Notice: Subject to any disclaimer, the term of this patent is extended or adjusted under 35 U.S.C. 154(b) by 0 days.

(21) Appl. No.: 10/626,345

(22) Filed: Jul. 23, 2003

(65) Prior Publication Data

US 2004/0158926 A1 Aug. 19, 2004

Related U.S. Application Data

(60) Provisional application No. 60/447,418, filed on Feb. 14, 2003.

(51) Int. Cl.[7] .............................................. A61G 13/12
(52) U.S. Cl. ...................... 5/621; 5/601; 5/623; 5/646
(58) Field of Search ............................. 5/621–624, 630, 5/632, 646, 659

(56) References Cited

U.S. PATENT DOCUMENTS

| | | | | | |
|---|---|---|---|---|---|
| 2,910,259 | A | * | 10/1959 | Johnson ...................... | 248/118 |
| 4,688,780 | A | * | 8/1987 | Hanz ............................. | 5/621 |
| 4,698,837 | A | * | 10/1987 | Van Steenburg ............ | 378/208 |
| 5,443,233 | A | * | 8/1995 | Kabanek ...................... | 248/118 |
| 5,642,541 | A | * | 7/1997 | Corbin ........................ | 5/507.1 |
| 5,675,851 | A | * | 10/1997 | Feathers ....................... | 5/632 |
| 6,101,650 | A | * | 8/2000 | Omdal et al. ................. | 5/623 |

* cited by examiner

*Primary Examiner*—Michael Trettel
(74) *Attorney, Agent, or Firm*—Thorpe North & Western

(57) ABSTRACT

A medical table extension device and method has an elongated plate with opposite attachment and support sections. The attachment section extends under a mattress of the medical table to be stabilized by a patient's body weight. The support section extends outwardly from the medical table to support a patient's limb. The plate can include a continuous sheet with at least one bend defining the attachment and support sections of the plate. The attachment and support sections can have upper surfaces disposed at different elevational heights.

22 Claims, 2 Drawing Sheets

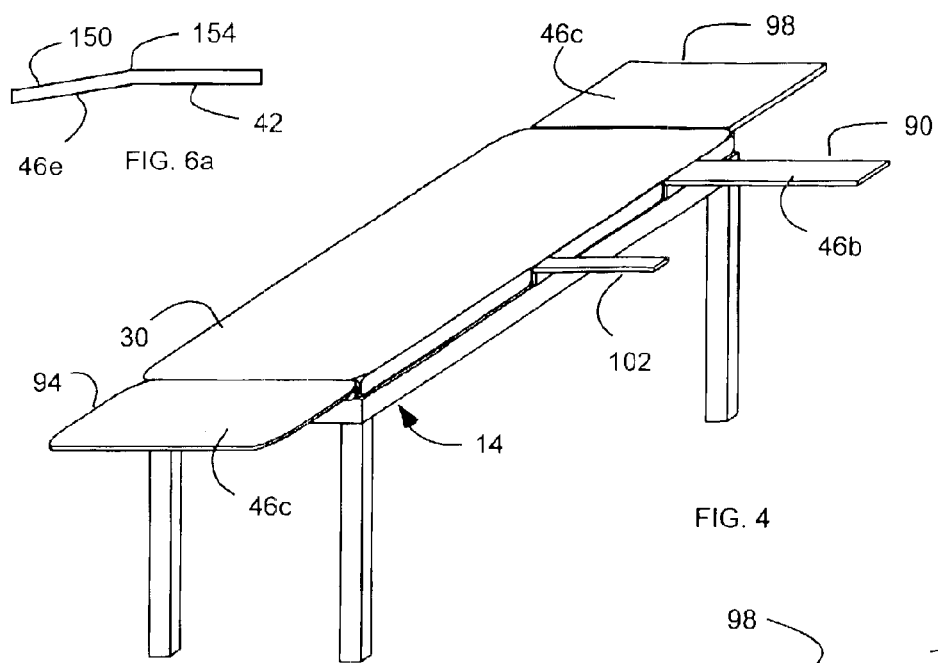
FIG. 6a
FIG. 4
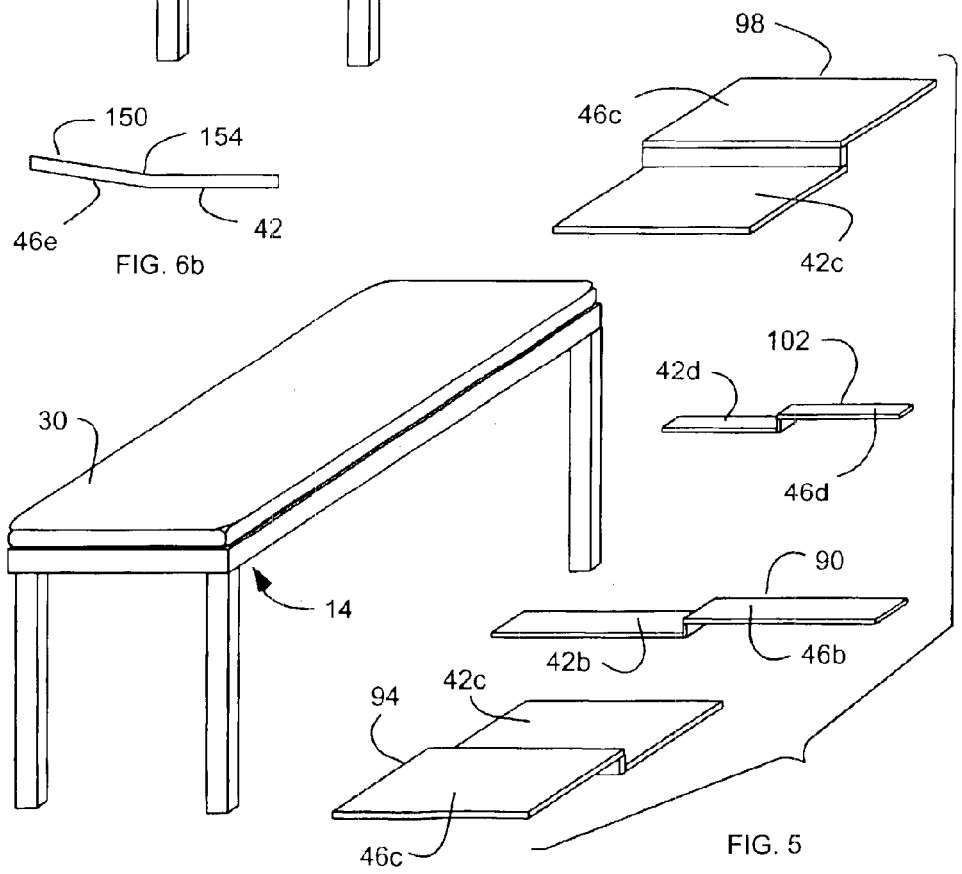
FIG. 6b
FIG. 5

MEDICAL TABLE EXTENSION AND METHOD

This application claims the benefit of U.S. Provisional Patent Application No. 60/447,418, filed Feb. 14, 2003.

BACKGROUND OF THE INVENTION

1. Field of the Invention

The present invention relates generally to a method and apparatus for extending a medical table to facilitate medical procedures and/or medical imaging.

2. Related Art

Various medical procedures and medical imaging often require a patient to be recumbent on a medical table, such as an operating table. Standard operating tables include metal tracks along either side to allow attachment of armboards. Such armboards include clamping mechanisms allowing the armboard to clamp onto the tracks of the table. Thus, a patient's arm can be extending from the medical table and onto the armboard for intravenous access, surgical intervention, and the like. Such armboards are often thick and include metal reinforcement. The configuration of such armboards is often incompatible with medical imaging. For example, with radiographic imaging, the metal reinforcement causes interference or obstruction with the image. Thus, the patient's arm is often repeatedly repositioned off the armboard to obtain unobstructed images. Repositioning consumes valuable operative time and compromises sterility. In addition, the thickness of the armboard positions the image intensifier away from the arm, reducing clarity. Similar problems exist with the medical table itself.

SUMMARY OF THE INVENTION

It has been recognized that it would be advantageous to develop a method and device to extend a patent's limb from a medical table without complicated attachment mechanisms, and without compromising medical imaging.

The invention provides a medical table extension device with an elongated plate having opposite attachment and support sections. The attachment section extends under a mattress of the medical table to be stabilized by a patient's body weight. The support section extends outwardly from the medical table to support a patient's limb.

In accordance with a more detailed aspect of the present invention, the plate can include a continuous sheet with at least one bend formed therein defining the attachment and support sections of the plate.

In accordance with another more detailed aspect of the present invention, the attachment and support sections can have upper surfaces disposed at different elevational heights.

The invention also provides a method for extending a table to facilitate a medical procedure. The method includes providing a table having a table surface and a mattress disposed on the table surface with a mattress surface to receive a patient. An attachment section of an elongated plate is disposed between the table surface and the mattress. A support section of the elongated plate is positioned adjacent the mattress with a support surface of the elongated plate substantially flush with the mattress surface. A patient is positioned over the mattress. A limb of the patient is positioned over the support section of the elongated plate.

The invention also provides a method for facilitating medical imaging. The method includes positioning a patient on a table. A limb of the patient is positioned over a support surface of an elongated plate extending from the table. The elongated plate is formed of an x-ray transparent material and has a lower surface and a thickness between the lower surface and the support surface less than approximately one inch. At least a portion of a medical imaging device is positioned adjacent the lower surface of the elongated plate.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 4 is a perspective view of a table extension system in accordance with an embodiment of the present invention;

FIG. 5 is a perspective exploded view of the table extension system of FIG. 4; and FIGS. 6a and 6b are side views of another table extension device in accordance with an embodiment of the present invention.

DETAILED DESCRIPTION

Figure 1:
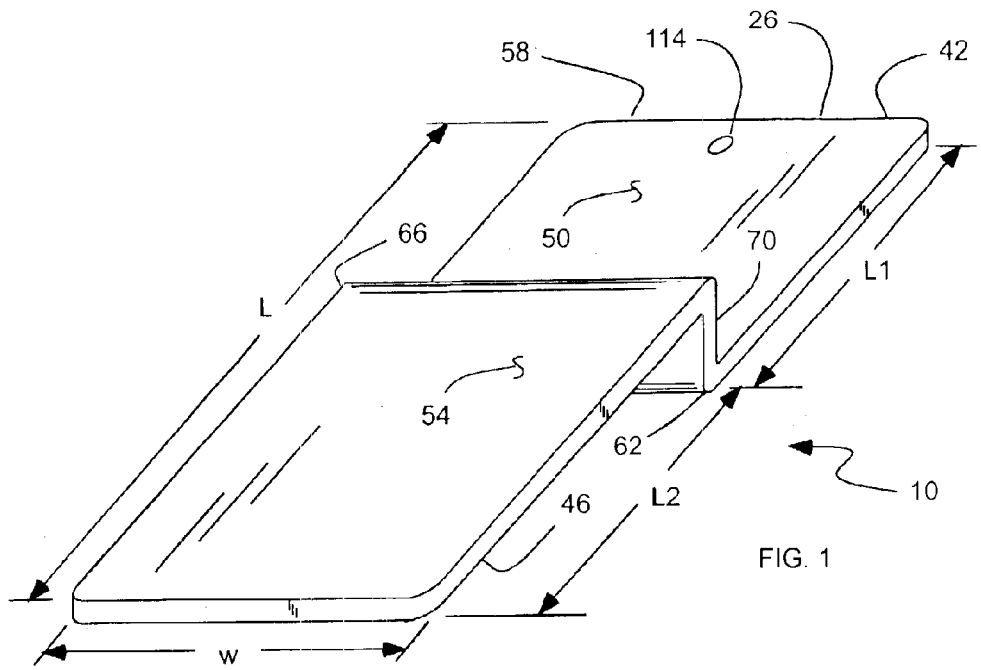
FIG. 1 is a perspective view of a table extension device in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Figure 2:
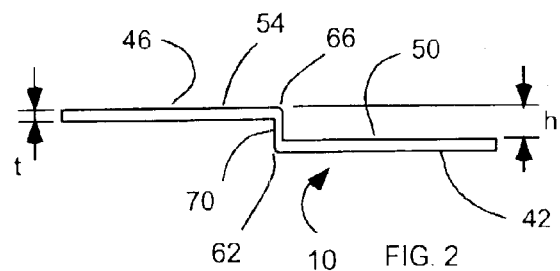
FIG. 2 is a side view of the table extension device of FIG. 1.
Figure 3:
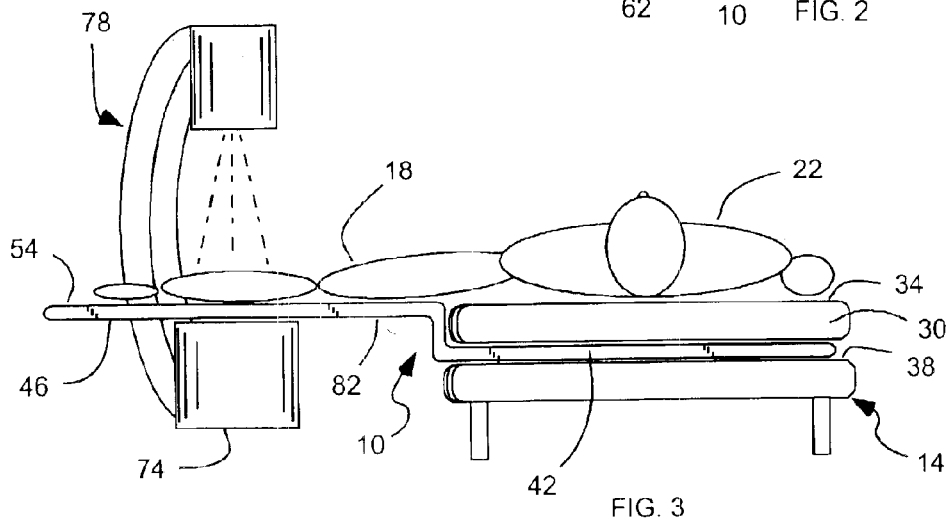
FIG. 3 is an end schematic view of the table extension device of FIG. 1 being used with a medical table and a medical imaging system.

As illustrated in FIGS. 1–3, a table extension device, indicated generally at 10, in accordance with an embodiment of the present invention is shown for extending a medical table 14 (FIGS. 3-5). The table extension device 10 can be used in surgical and medical imaging operations to extend a portion of the medical table 14, and to receive a limb 18 (FIG. 3) or other portion of a patient 22 (FIG. 3). As used herein, the term "limb" refers broadly to a portion or portions of a patient's body, including a patient's arm, hand, leg, foot, head, or torso. The table extension device 10 can be used in surgical operations to position the patient's limb in a more convenient or accessible position. For example, the patient's limb 18, such as the arm, can be positioned on the table extension device 10, as shown in FIG. 3, for surgery on some portion of the patient's limb. As another example, the patient's arm can be positioned on the table extension device 10 for accommodating intravenous lines or other equipment. The table extension device 10 can also be used in medical imaging, either during or separate from surgical operations, to facilitate imaging. For example, the patient's limb 18, such as the arm, can be positioned on the table extension device 10, as shown in FIG. 3, with a portion of the medical imaging system, such as the image intensifier, adjacent to the table extension device, as described in greater detail below.

Referring to FIG. 3, the medical table 14 can include a mattress 30 with an upper or support surface 34. The mattress 30 can be disposed on an upper surface 38 of the table 14. Such medical tables are known to those skilled in the art. The term "medical table" is used herein broadly to refer to various different types of tables or supports used in medical facilities, operating rooms, etc., including operating tables, x-ray tables, etc. The mattress 30 can be flexible, and can have a thickness of approximately two inches.

Referring again to FIGS. 1–3, the table extension device 10 includes an elongated plate 26 with opposite attachment and support sections 42 and 46. The attachment section 42 is capable of extending under the mattress 30 of the medical table 14, and can be stabilized by body weight of the patient 22. The support section 46 can extend outwardly from the medical table 14 to support a patient's limb 18. Thus, the plate 26 can be cantilevered, with the patient's own body weight counterbalancing or stabilizing their limb, without the use of mechanical attachments. Alternatively, simple clamps can also be used to clamp the attachment section 42 to the table 14. It will be appreciated that the plate 26 or attachment section 42 can be positioned anywhere along the medical table 14, and can be easily positioned or repositioned.

The attachment and support sections 42 and 46 can have upper surfaces 50 and 54 disposed at different elevational heights h. The upper surface 54 of the support section 46 can be disposed at an elevational height h above the upper surface 50 of the attachment section 42. The elevational height h can be the same as, or substantially equal to, the thickness of the mattress 30, such as approximately two inches. Therefore, the upper surface 54 of the support section 46 can be substantially flush with the upper surface 34 of the mattress 30, as shown in FIG. 3. Having the upper surface 54 of the support section 46 flush with the upper surface 34 of the mattress 30 can provide greater comfort to the patient 22.

The elongated plate 26 can include, or can be formed of, a continuous sheet 58. The continuous sheet 58 can be a single, continuous, integral sheet, and can be formed from a single sheet of material. One or more bends can be formed in the sheet 58 between the attachment and support sections 42 and 46, and can form the elevational height h between the upper surfaces 50 and 54 of the attachment and support sections 42 and 46. For example, the sheet 58 can include at least first and second, or upper and lower, bends 62 and 64. The bends 62 and 64 can be substantially right angle bends (or substantially 90 degree bends) oriented in opposite directions.

An intermediate section 70 can be formed intermediate the bends 62 and 64, and the attachment and support sections 42 and 46. The intermediate section 70 can be oriented substantially transverse to both the attachment and support sections 42 and 46. For example, the intermediate section 70 can be substantially orthogonal to the attachment and support sections 42 and 46. Thus, the intermediate section 70 forms a transition between the attachment and support sections 42 and 46, and allows the upper surfaces to be at different elevational heights. In addition, the intermediate section 70, and its orientation, allows the support section 46 to abut to the mattress for patient comfort and ease of use.

The orientation and position of the attachment, support and intermediate sections 42, 46 and 70 provide the plate 26 or sheet 58 with a profile or cross-section shaped as a short, wide, block "s" or "z". The attachment and support sections 42 and 46 can be substantially planar, and can be substantially parallel with one another without being coplanar (or being substantially non-coplanar). Thus, the support section 46 can be substantially parallel and flush with the upper surface 34 of the mattress 30, while the attachment section 42 can be positioned between the mattress 30 and table 14, and thus parallel with both. It will be appreciated that during use, the plate 26 or sheet 58, or the support section 46, may bend under the weight of the user's limb.

In addition, the plate 26 or sheet 58 can have a substantially constant thickness t (FIG. 2). Thus, the plate 26 can be formed from a single sheet of material. Furthermore, the plate 26 or sheet 58 can be relatively thin, such as less than one inch thick. Or at least the support section 46 can have a thickness less than one inch. It will be appreciated that having a thinner support section 46 can allow medical imaging equipment to be positioned closer to the limb 18. For example, as shown in FIG. 3, an image intensifier 74 of an x-ray or c-arm system 78 can be positioned adjacent a lower surface 82 of the support section 46, and thus within approximately one inch of the patient's limb 18. It will be appreciated by those skilled in the art that positioning the image intensifier 74 closer to the patient's limb can result in larger and clearer images. Thicker supports can increase the magnification and distort the image. In addition, the space above the patient's limb is also greater, facilitating operations. Thus, the support section 46 has a slender profile that preserves working space, facilitates larger and clearer images, and allows real-time imaging. Thus, the c-arm or x-ray system 78 can be "parked," permitting real-time imaging.

The support section 46 can be formed of an x-ray transparent material. Thus, images can be taken through the support section 46, and without moving the patient's limb 18 from the support section 46. Again, it will be appreciated by those skilled in the art that imaging without repositioning the patient's limb results in greater efficiency and sterility. Because the plate 26 or sheet 58 can be formed of a single, continuous sheet, the entire plate 26 or sheet 58 can be formed of an x-ray transparent material. The sheet 58 can be a sheet of acrylic, such as Plexiglas®. In addition, the sheet 58 or plate 26 can be substantially clear or transparent. The transparent plate 26 can facilitate positioning of the imaging equipment, such as the image intensifier. In addition, indicia can be formed on the lower surface 82 and visible through the upper surface 54 but without interfering with the upper surface. The indicia can include instructions or warnings, indicators, alignment or positioning marks, scales, etc.

The size and shape of the plate 26 or sheet 58 can be configured for the particular use or limb to be supported. Thus, the plate 26 or sheet 58 can have a length L between approximately one to five feet, and a width w between approximately two inches to three feet. The attachment section 42 can have a length L1 that extends substantially across a width of the table, or approximately two-and-a-half feet. The support section 46 can have a length L2 configured for the limb to be supported, or between approximately six inches to two-and-a-half feet. The lengths L1 and L2 of the attachment and support sections 42 and 46 can be substantially equal, so that either end can be used for either attachment or support, or they can be different, such as with the length L1 of the attachment section 42 configured to extend substantially under the patient, and the length L2 of the support section 46 configured to extend only as long as needed.

Referring to FIGS. 4 and 5, the table extension device 10 can be sized and shaped for a particular limb. For example, the table extension device 10 can be an armboard extension 90 designed to extend laterally from a lateral side of the medical table 14. A support section 46b of the armboard extension 90 can have a length sized to receive a patient's arm, or between approximately two to three feet long. An attachment section 42b of the armboard extension 90 can have a length substantially equal to the support section 46b so that the sections can be interchangeable, or can have a length to extend substantially across the width of the table 14.

As another example, the table extension device 10 can be a footboard or headboard extension 94 or 98 designed to extend longitudinally from an end of the medical table 14. A support section 46c can have a length sized to receive a patient's foot or head, or between approximately one to two feet, and a width spanning the width of the table, or between approximately two to three feet. An attachment section 42c can have a length substantially equal to the support section 46c so that the sections can be interchangeable, or can have a length sufficient to be counterbalanced by the patient.

As another example, the table extension device 10 can be a body cast support or spica support 102 configured to extend laterally from a side of the table. The body cast support 102 can include a support section 46d that forms a slender tongue to support the patient's back or spine and pelvis while a cast is wrapped around the patient's torso and legs. An attachment section 42d can be stabilized by a clamp. The patient can be positioned on the table, with their spine and pelvis on the support section 46d. An assistant can hold the patient's legs while a body cast is wrapped around the patient's torso and legs. In addition, an imaging system or c-arm 78 can be parked over the patient's pelvis, permitting real-time imaging to ascertain alignment of the patient's hips and femora.

A table extension system 110 can include a plurality of different table extension devices, or a plurality of separate, elongated plates. For example, the system 110 can include at least an armboard extension 90 and a footboard or headboard extension 94 or 98. As another example, the system 110 can also include a body cast support or spica support 102. Various different table extension devices of various different sizes and configurations can be provided. Thus, a number of different table extension devices can be provided in a set to accommodate the most common or frequent operations or situations. Because the table extension devices are thin, they can be easily and efficiently stored. For example, the table extension devices can be stacked and stored on a shelf, or in a closet. As another example, the table extension devices can be hung from a rack or the like on the wall. The table extension devices can be provided with an aperture 114 (FIG. 1) to receive a peg or hook of a rack on the wall.

A method for extending a medical table 14 to facilitate a medical procedure, such as surgery and/or imaging, or for using the table extension device 10 described above, includes providing a table 14 having a table surface 38, and a mattress 30 disposed on the table surface 38 with a mattress surface or upper surface 34 to receive a patient 22 thereon. An attachment section 42 of an elongated plate 26 is disposed or inserted between the table surface 38 and the mattress 30. A support section 46 of the elongated plate 26 is positioned adjacent the mattress 30 with a support surface or upper surface 54 of the elongated plate 26 substantially flush with the upper surface 34. A patient 22 is positioned over or on the mattress 30. The attachment section 42 can be inserted under the mattress 30 while the patient 22 is on the mattress 30, or before the patient is placed on the mattress. A limb 18 of the patient 22 is positioned over or on the support section 46 of the elongated plate 26.

In the case of an armboard extension 90 (FIGS. 4 and 5), the plate 26 can be positioned on a side of the table 14, and oriented to extend laterally outwardly from the table. The patient's limb 18 can be extended laterally outwardly past the table and over the plate 26 or support section 46. In the case of a footboard or headboard extension 94 or 98, the plate 26 can be positioned at the end (head or foot) of the table 14, and oriented to extend longitudinally outwardly from the table. The patient's foot or head can be extended longitudinally outwardly past the table 14 and over the plate 26 or support section 46.

A medical procedure can be performed with the patient's limb disposed on the table extension device. The medical procedure can include, for example, surgery, x-rays, etc. A medical imaging device, or portion thereof, can be positioned adjacent a lower surface 82 of the support section 46. For example, an image intensifier 74 of an x-ray or c-arm system 78 can be positioned under the support section 46, and adjacent the lower surface 82 of the support section 46, as shown in FIG. 3. Because the support section 46 is x-ray transparent, the patient's limb can remain on the support section 46 during imaging, resulting in greater efficiency and sterility. Because the support section 46 is thin (less than approximately one inch), the image intensifier 74 can be positioned closer to the patient's limb, resulting in greater image clarity. In addition, the thinness of the support section 46 creates a greater space above the patient's limb, resulting in easier and more convenient access to the patient's limb during the medical procedure. Therefore, the imaging system or c-arm 78 can be "parked" about the patient's limb during the medical prodecure.

A method for facilitating medical imaging, or for using the table extension device 10 described above, includes positioning a patient 22 on a table 14. A limb 18 of the patient 22 is positioned over a support surface or upper surface 54 of an elongated plate 26 or support section 46 extending from the table 14. The elongated plate 26 or support section 46 is formed of an x-ray transparent material, and has a thickness less than approximately one inch. A medical imaging device, or portion thereof, is positioned adjacent the lower surface 82 of the elongated plate 26 or support section 46. As discussed above, because the support section 46 is x-ray transparent, the patient's limb can remain on the support section 46 during imaging, resulting in greater efficiency and sterility. Because the support section 46 is thin (less than approximately one inch), the image intensifier 74 can be positioned closer to the patient's limb, resulting in greater image clarity. In addition, the thinness of the support section 46 creates a greater space above the patient's limb, resulting in easier and more convenient access to the patient's limb during the medical procedure. Therefore, the imaging system or c-arm can be "parked" about the patient's limb during the medical prodecure.

Referring to FIGS. 6a and b, another table extension device 150 similar to those described above can have attachment and support sections 42 and 46e. The sections can be substantially planar, and can have a bend 154 oriented at an oblique angle with respect to one another. The device 150 can be oriented so that the support section 46e is angled upwardly or downwardly to facilitate the medical procedure being performed.

It is to be understood that the above-referenced arrangements are only illustrative of the application for the principles of the present invention. Numerous modifications and alternative arrangements can be devised without departing from the spirit arid scope of the present invention while the present invention has been shown in the drawings and fully described above with particularity and detail in connection with what is presently deemed to be the most practical and preferred embodiments(s) of the invention, it will be apparent to those of ordinary skill in the art that numerous modifications can be made without departing from the principles and concepts of the invention as set forth in the claims.

What is claimed is:

1. A table extension system configured to extend a medical table, comprising:
   a) a plurality of separate, elongated plates including at least:
      i) an armboard extension configured to extend laterally from a lateral side of the medical table; and
      ii) a footboard or headboard extension configured to extend longitudinally from an end of the medical table;
   b) each of the plates having opposite attachment and support sections, the attachment section being configured to extend under a mattress of the medical table and to be stabilized by a patient's body weight, and the support section being configured to extend outwardly from the medical table to support a patient's limb; and
   c) the support section of the footboard or headboard extension having a width substantially equal to a width of the medical table; and
   d) the support section of the armboard extension having a length substantially equal to the width of the medical table.

2. A system in accordance with claim 1, wherein each of the plates includes a continuous sheet having at least one bend between the attachment and support sections.

3. A system in accordance with claim 1, wherein the attachment and support sections of each of the plates have upper surfaces disposed at different elevational heights.

4. A table extension device configured to extend a medical table, comprising:
   a) an elongated plate including a continuous sheet with at least one bend formed therein defining opposite attachment and support sections of the plate, the attachment section being configured to extend under a mattress of the medical table and to be stabilized by a patient's body weight, and the support section being configured to extend outwardly from the medical table to support a patient's limb;
   b) the attachment and support sections having upper surfaces disposed at different elevational heights; and
   c) the attachment and support sections have a substantially constant and equal thickness less than approximately one inch; and
   d) the attachment support sections are planar.

5. A method for extending a table to facilitate a medical procedure, comprising the steps of:
   a) providing a table having a table surface and a mattress disposed on the table surface with a mattress surface configured to receive a patient;
   b) providing an elongated plate with attachment and support sections that are substantially planar and are oriented at an oblique angle with respect to one another;
   c) disposing the attachment section of the elongated plate between the table surface and the mattress;
   d) positioning a patient over the mattress; and
   e) positioning a limb of the patient over the support section of the elongated plate.

6. A method in accordance with claim 5, further comprising the steps of:
   providing a plate with the support section being formed of an x-ray transparent material; and
   positioning at least a portion of a medical imaging device adjacent a lower surface of the support section.

7. A method in accordance with claim 5, further comprising the step of:
   providing a plate including a continuous sheet having at least one bend between the attachment and support sections.

8. A method in accordance with claim 5, further comprising the step of:
   providing a plate including a continuous sheet having at least two bends between the attachment and support sections, and an intermediate section intermediate the attachment and support sections, oriented substantially transverse to both the attachment and support sections.

9. A method in accordance with claim 5, further comprising the step of:
   providing a plate that has a substantially constant thickness.

10. A method in accordance with claim 5, further comprising the steps of:
    providing the plate with the attachment and support sections having upper surfaces disposed at different elevational heights; and
    disposing at least a portion of the upper surface of the support section at an elevational height above the upper surface of the attachment section, the elevational height being substantially equal to a thickness of the mattress disposed on the medical table, and at least a portion of the upper surface of the support section being substantially flush with the support surface of the mattress.

11. A method in accordance with claim 5, further comprising the step of:
    positioning the support section of the elongated plate adjacent the mattress with at least a portion of a support surface of the elongated plate substantially flush with the mattress surface.

12. A method for facilitating medical imaging, comprising the steps of:
    a) positioning a patient on a table;
    b) providing an elongated plate with attachment and support sections that are substantially planar and are oriented at an oblique angle with respect to one another;
    c) positioning a limb of the patient over the support surface of the elongated plate extending from the table, the elongated plate being formed of an x-ray transparent material and having a lower surface and a thickness between the lower surface and the support surface less than approximately one inch; and
    d) positioning at least a portion of a medical imaging device adjacent the lower surface of the elongated plate.

13. A method in accordance with claim 12, further comprising the steps of:
    a) disposing the attachment section of the elongated plate between an upper surface of the table and a mattress disposed on the table; and
    b) positioning the support section of the elongated plate adjacent the mattress with at least a portion of the support surface of the elongated plate substantially flush with an upper surface of the mattress.

14. A method in accordance with claim 12, further comprising the step of:

providing a plate including a continuous sheet having at least one bend between the attachment and support sections.

15. A method in accordance with claim 12, further comprising the step of:

providing a plate including a continuous sheet having at least two bends between the attachment and support sections, and an intermediate section intermediate the attachment and support sections, oriented substantially transverse to both the attachment and support sections.

16. A method in accordance with claim 12, further comprising the step of:

providing a plate that has a substantially constant thickness.

17. A method in accordance with claim 12, further comprising the steps of:

providing a plate with the attachment and support sections having upper surfaces disposed at different elevational heights; and disposing at least a portion of the upper surface of the support section at an elevational height above the upper surface of the attachment section, the elevational height being substantially equal to a thickness of the mattress disposed on the medical table, and at least a portion of the upper surface of the support section being substantially flush with the support surface of the mattress.

18. A table extension device configured to extend a medical table, comprising:

a) an elongated plate having opposite attachment and support sections, the attachment section being configured to extend under a mattress of the medical table and to be stabilized by a patient's body weight, and the support section being configured to extend outwardly from the medical table to support a patient's limb; and b) the support section being formed of an x-ray transparent material and having a thickness less than approximately one inch; and c) the attachment and support sections are planar.

19. A table extension device configured to extend a medical table, comprising:

an elongated plate including a continuous sheet with at least one bend formed therein defining opposite attachment and support sections of the plate, the attachment section being configured to extend under a mattress of the medical table and to be stabilized by a patient's body weight, and the support section being configured to extend outwardly from the medical table to support a patient's limb;

the support section of the plate having a width substantially equal to a width of the medical table.

20. A table extension system configured to extend a medical table, comprising:

a) a plurality of separate, elongated plates;

b) each of the plates having opposite attachment and support sections, the attachment section being configured to extend under a mattress of the medical table and to be stabilized by a patient's body weight, and the support section being configured to extend outwardly from the medical table to support a patient's limb; and c) the support sections of the plurality of plates having different lengths and widths with respect to one another.

21. A system in accordance with claim 20, wherein each of the plates includes a continuous sheet having at least one bend between the attachment and support sections.

22. A system in accordance with claim 20, wherein the attachment and support sections of each of the plates have upper surfaces disposed at different elevational heights.

* * * * *